Figure 1:
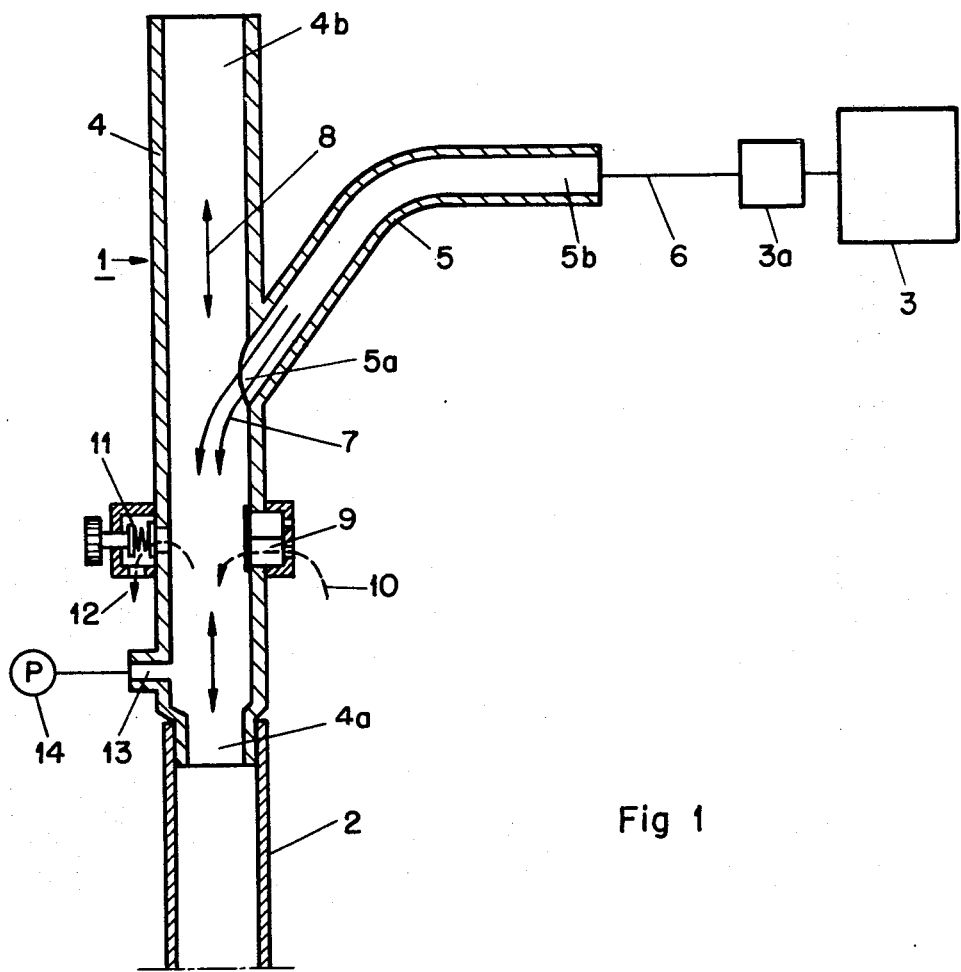

United States Patent [19]

Sjöstrand

[11] 3,993,059

[45] Nov. 23, 1976

[54] DEVICE FOR VENTILATING A PATIENT

[75] Inventor: Ulf Hakän Sjöstrand, Orebro, Sweden

[73] Assignee: AGA Aktiebolag, Lidingo, Sweden

[22] Filed: Nov. 13, 1974

[21] Appl. No.: 523,409

[30] Foreign Application Priority Data

Nov. 13, 1973    Sweden .............................. 7315392

[52] U.S. Cl. .......................... 128/145.8; 128/145.7
[51] Int. Cl.² ....................................... A61M 16/00
[58] Field of Search ..................... 128/145.5–145.8, 128/351, 203, 142, 142.2, 142.3, 209, 210, 146.5, 147; 137/604

[56] References Cited
UNITED STATES PATENTS

| | | | |
|---|---|---|---|
| 2,121,311 | 6/1938 | Anderson et al. | 128/145.8 |
| 2,834,339 | 5/1958 | Bennett et al. | 128/145.7 |
| 3,006,337 | 10/1961 | Aguado | 128/145.5 |
| 3,039,469 | 6/1962 | Fountain | 128/351 |
| 3,073,298 | 1/1963 | Stanton | 128/145.8 |
| 3,262,446 | 7/1966 | Stoner | 128/145.8 |
| 3,474,785 | 10/1969 | Jansson | 128/145.8 |
| 3,605,751 | 9/1971 | Gulling | 128/351 |
| 3,643,686 | 2/1972 | Koegel | 128/145.5 |
| 3,731,691 | 5/1973 | Chen | 128/351 |

FOREIGN PATENTS OR APPLICATIONS

| | | | |
|---|---|---|---|
| 1,207,395 | 2/1960 | France | 128/145.5 |
| 1,270,946 | 4/1972 | United Kingdom | 128/351 |

*Primary Examiner*—Robert W. Michell
*Assistant Examiner*—Henry J. Recla
*Attorney, Agent, or Firm*—Larson, Taylor and Hinds

[57] ABSTRACT

A device for ventilating a patient by means of a lung ventilator which comprises a gas source and a controlled valve arrangement for intermittent feeding of breathing gas from the gas source. A connecting piece is mounted on an endotracheal tube or a tracheal cannula inserted into the trachea of the patient. Said piece comprises a substantially straight main tube and a branch tube and the junction between these tubes is so designed that it has a pneumatic valve function, whereby essentially the entire quantity of the breathing gas supplied from the lung ventilator to the branch tube is conducted towards said one end of the main tube, whereas gas flow, uneffected by breathing gas that may be blown into the branch tube, is allowed in both directions through the main tube past the orifice of the branch tube into the main tube.

2 Claims, 2 Drawing Figures

DEVICE FOR VENTILATING A PATIENT

The present invention refers to a device for connecting a patient by means of an endotracheal tube or a tracheal cannula to a lung ventilator which comprises a gas source for the desired breathing gas and a controlled valve device for intermittent and periodic feeding of breathing gas from the gas source. The device according to the invention is especially intended for the connection of a patient to a lung ventilator which is designed for high frequency over-pressure ventilation, so called HFPPV, but the device according to the invention may also be used in other types of lung ventilators.

When ventilating a patient by means of a lung ventilator it is desired to have a considerably greater freedom as to the treatment of the patient than what is possible when using the ventilation devices available before. Thus it is exceedingly desirable that during the ventilaton by means of the ventilator, the patient has also the possibility to breathe spontaneously and that the spontaneous breathing is not prevented by or in conflict with the ventilation by means of the ventilator used. Further it would be of great advantage, if during the ventilation of the patient, instruments could be inserted into the trachea of the patient, especially for cleaning the air-passages of the patient but in certain cases also for other purposes, such as for taking samples or for observation of the air-paassages. Further it is desirable to be able to work with a variably adjustable positive end expiratory pressure, i.e. an adjustable overpressure at the end of the expiration phase of the ventilation. It should also be of advantage if, during the ventilation of the patient by means of an automatically working ventilator, it would be possible to ventilate the patient manually by means of a rubber bag, bellows or the like, without this manual ventilation coming into conflict with the function of the lung ventilation. In modern respirator attendance it has proved to be desirable to pass quickly and in a simple manner from a positive ventilation of the patient by means of the automatically working ventilator used to a treatment according to the so called CPAP (continuous positive airway pressure), which means that the patient is continuously supplied with desired breathing gas under a predetermined overpressure but that the patient himself has to do the breathing work by means of spontaneous breathing. Then there is of course the always existing claim, that the ventilation of the patient shall be carried out in a way ensuring complete safety for the patient.

None of the ventilation devices known before gives all the abovementioned possibilities and therefore the object of the present invention is to produce a device for connecting a patient to a lung ventilator, by means of which device all the abovementioned functions are possible to achieve.

The primary features of the device according to the invention will be evident from the characterizing part of the annexed claims.

The connection part between the main tube and the branch tube of the device may preferably be designed such that one end of the branch tube is connected to the wall of the main tube in such a way that an acute angle is formed between the axial direction of the main tube and the axial direction of the branch tube near the junction and so that the orifice of the branch tube into the main tube is directed substantially towards said one end of the main tube. In addition, the main tube preferably is substantially straight and has a completely open inner passage in all its length between both ends.

By means of a device according to the invention a patient can be ventilated by means of the ventilator connected, in that the breathing gas from the ventilator is intermittently fed through the branch tube into the main tube, whereby due to the special design of the connection part between the branch tube and the main tube essentially all the breathing gas is automatically fed to the end of the main tube, which is connected to the endotracheal tube or tracheal cannula inserted into the patient. During the ventilation by means of the lung ventilator the patient may breathe spontaneously through the main tube which is open in all its length and besides it is possible through this tube to insert instruments into the trachea of the patient without disturbing the ventilation by means of the lung ventilator.

Advantageous embodiments and developments of the device according to the invention can be designed in accordance with the attached claims.

Figure 2:
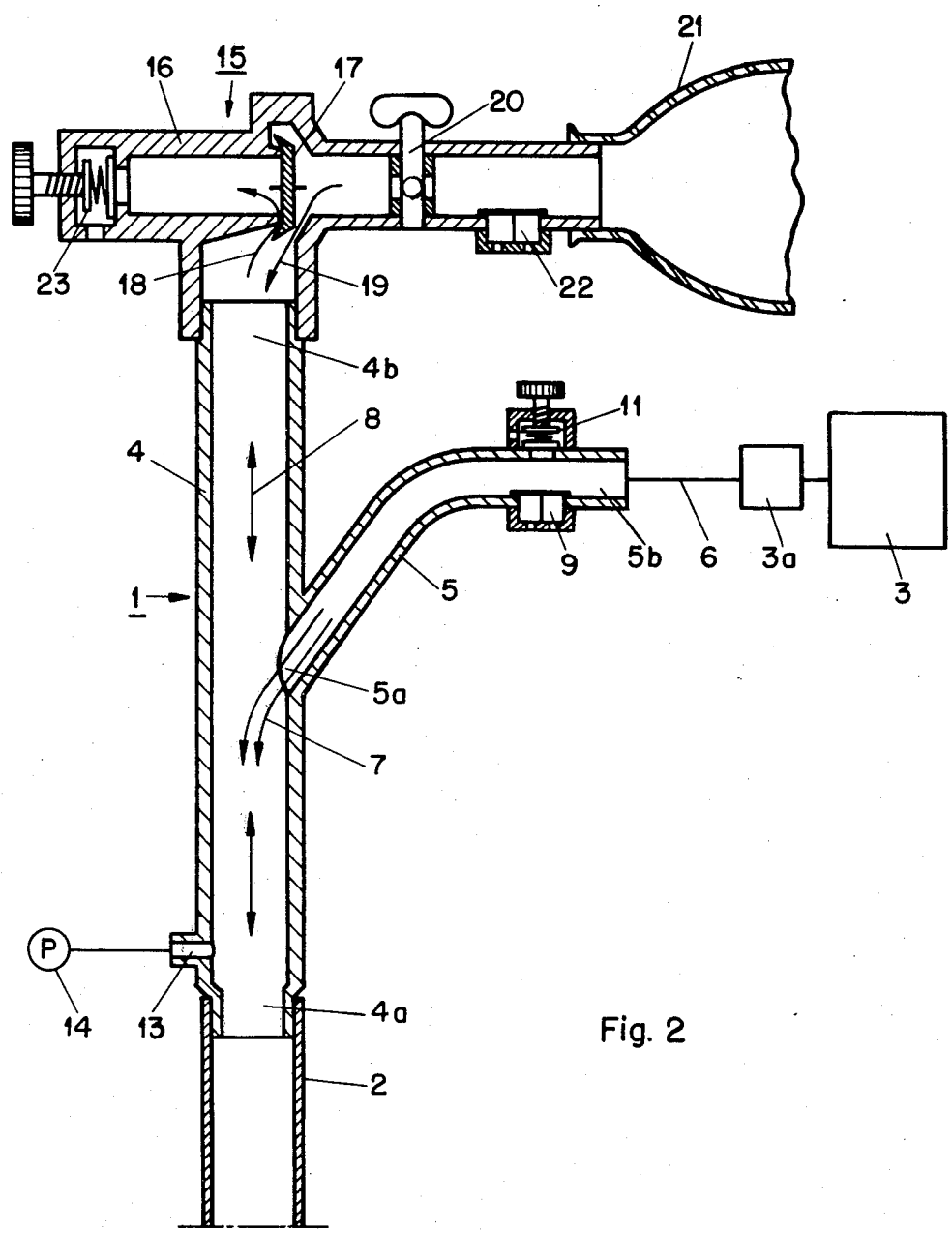

In the following the invention will be described in detail in connection with the attached drawing, which illustrates some embodiments of the invention, whereby FIG. 1 schematically shows a first embodiment of arrangement according to the invention, which allows ventilation of the patient by means of a lung ventilator connected to the patient and simultaneously spontaneous breathing of the patient as well as insertion of instruments in the trachea of the patient and FIG. 2 schematically shows a further arrangement according to the invention, which moreover allows variable adjustment of the end expiratory pressure, manual ventilation of the patient and a CPAP treatment.

The arrangement according to the invention, schematically and as an example shown in FIG. 1, comprises a common connection piece designated 1 between an endotracheal tube or tracheal cannula 2 inserted into the trachea of the patient and the utilized lung ventilator 3. The lung ventilator 3 can in principle be of an arbitrary kind, but is assumed, for simplicity's sake, in the following description to be of a type designed for HFPPV ventilation. The lung ventilator 3 is in principle of a conventional type and comprises a gas source for the desired breathing gas (with necessary arrangements for determining the composition of the breathing gas, temperature, content of humidity and pressure) and a controlled valve arrangement 3a for intermittent feeding of the breathing gas with a desired, usually variably adjustable frequency and variably adjustable relation between the length of each such gas feeding and the length of the intermediate intervals.

The connecting piece 1 according to the invention comprises a main tube 4, the one end 4a of which is connected to the endotracheal tube or tracheal cannula 2 inserted into the patient, and a branch tube 5 the one end 5a of which emerges into the main tube 4, whereas its other end 5b is connected to the utilized ventilator 3 via a suitable conduit 6 only schematically shown in the drawing.

The connection part between the main tube 4 and the branch tube 5 is so designed that it functions as a pneumatic valve which permits essentially all the quantity of the gas that flows from the ventilator 3 through the branch tube 5 into the main tube 4 in the direction towards the lower end 4a of the main tube, as indicated by the arrows 7. Furthermore, free gas flow is allowed in both directions through the main tube 4 past the orifice 5a of the branch tube 5, as indicated by the arrows 8.

Thus, during the insufflation period of the work cycle of the ventilator 3, breathing gas is flowing from the ventilator 3 through the branch tube 5 and furtheron through the lower part of the main tube 4 into the endotracheal tube or tracheal cannula 2 and into the lungs of the patient. During the following exsufflation period of the work cycle of the ventilator 3, during which no breathing gas is fed from the ventilator, the consumed breathing gas will, due to the elasticity of the lungs of the patient, be pressed out of the lungs through the endotracheal tube 2 and further through the main tube 4 in the connection piece 1 and out into the surrounding atmosphere at the upper end 4b of the main tube. It is realized that this ventilation of the patient by means of the lung ventilator 3 may proceed unobstructed even if an instrument is simultaneously inserted into the trachea of the patient through the main tube 4 of the connection piece 1 and the endotracheal tube 2 for instance for sucking clean the air-passages of the patient.

Furthermore, if the patient so wishes, he can breathe spontaneously through the main tube 4 of the connection piece 1 without this spontaneous breathing being in any way conflicted by the ventilation going on by means of the ventilator 3. As a matter of fact, if the spontaneous exhalation of the patient should coincide with an insufflation phase of the ventilator 3, during which breathing gas is supplied to the branch tube 5 from the ventilator, then breathing gas flowing from the branch tube 5 into the main tube 4 will be influenced by the spontaneous expiration of the patient and turned off upwards in the direction towards the upper end 4b of the main tube 4, so that the breathing gas supplied from the branch tube 5 as well as the gas spontaneously exhaled by the patient flow out from the upper part 4b of the main tube 4. Thus, the patient has full possibility to breathe spontaneously during the ventilation by the ventilator 3.

The wall of the main tube 4 is provided with a diaphragm valve 9 functioning as a non-return valve, which only allows the flowing-in of air from the surrounding atmosphere into the main tube 4. When breathing spontaneously it is possible for the patient to inhale air through this non-return valve 9 as indicated by the dashed arrow 10, if the upper end 4b of the main tube 4 should be closed either unintendedly or deliberately, in accordance with a further development of the invention which will be described in the following.

The wall of the main tube 4 is also provided with an overpressure valve 11 having an adjustable opening pressure, which allows flowing out of gas from the interior of the main tube 4 to the surrounding atmosphere, if the pressure inside the lower part of the main tube 4 is higher than the set opening pressure of the valve. This overpressure valve 11 has a double function. On one hand it guarantees that during the insufflation period of the ventilator 3 the pressure at the upper end of the endotracheal tube 2 does not exceed a desired maximum value. On the other hand it makes possible the exhalation of the patient, as marked by means of the dashed arrow 12, if the upper end 4b of the main tube 4 should be closed for one of the reasons mentioned above.

As well the nonreturn valve 9 as the overpressure valve 11 may alternately be placed in the branch tube 5 instead of in the lower part of the main tube 4. It may be of advantage to place these valves in the branch tube 5, especially in an arrangement intended to be used for babies, since here the shortest possible exhalation passage from the patient is desired, viz a short main tube 4.

The lower part of the main tube 4 is also provided with a recess 13 for the connection to a manometer 14 for measuring and registering or for indicating the pressure at the upper end of the endotracheal tube 2.

The simple device according to the invention, shown in FIG. 1 and described above, allows positive ventilation, for instance HFPPV ventilation of a patient by means of a suitable ventilator, simultaneously as the patient has the possibility to breathe spontaneously, and an instrument can be inserted into the trachea of the patient. On the other hand, this simple device does not allow an adjustment of an end expiratory overpressure, a CPAP treatment or a manual ventilation of the patient. This is however possible by means of the further development of the device shown schematically and as an example in FIG. 2.

The connection piece 1, shown in FIG. 2, consisting of the main tube 4 and the branch tube 5 is designed in exactly the same way as in FIG. 1 except that the nonreturn valve 9 and the overpressure valve 11 are located in the branch tube 5 instead of in the main tube 4. Also in the embodiment shown in FIG. 2 the nonreturn valve 9 and the overpressure valve 11 could be arranged at the lower part of the main valve 4.

The lower end 4a of the main tube 4 is, as before, connected to the endotracheal tube 2 inserted in the patient, whereas the outer end 5b of the branch tube 5, by means of the conduit 6, is connected to the lung ventilator 3 and its controlled intermittently working valve 3a.

The upper end 4b of the main tube 4, on the other hand, does not longer open directly to the surrounding atmosphere but is connected to a valve device, generally designated 15, detachably mounted on the main tube 4. The valve housing 16 of the device 15 is substantially designed as a T-tube, which in its diverging point cmprises an automatically working two phase three-way diaphragm valve 17, which allows alternatively gas to flow from the main tube 4 into the left part of the valve housing 16, as indicated by an arrow 18, if the gas pressure in the upper end of the main tube 4 is higher than inside the valve housing 16, or gas to flow into the upper part of the main tube from the right part of the valve housing 16, as indicated by an arrow 19, if the gas pressure in the right part of the valve housing 16 is higher than in the upper part of the main tube 4. The right part as shown in FIG. 2 of the valve housing 16 is provided with a shut-off valve 20 which in the embodiment shown is manually controllable, and is connected to a rubber bag 21 or the like of the kind normally used for manual ventilation of a patient. Further, between the shut-off valve 20 and the rubber bag 21 there is a suction valve 22 for sucking in gas into the rubber bag 21. This suction valve 22 can be in communication with the surrounding atmosphere, as shown in the drawing, or can in a conventional manner be connected to a suitable oxygen source, if the manual ventilation shall be made with other gas than air.

The left part as shown in FIG. 2 of the valve housing 16 is provided with an overpressure valve 23 having a variably adjustable opening pressure. This overpressure valve 23 serves as an exhalation valve and can either communicate with the surrounding atmosphere as shown in the drawing, or be connected to a suitable conventional gas volume meter for measuring the gas volume exhaled.

If the shut-off valve 20 is in its closed position viz. no manual ventilation of the patient is desired, the ventilation of the patient will be carried out by means of the lung ventilator 3 in the manner described above in connection with FIG. 1, whereby during the exsufflation period of the ventilator 3 the consumed breathing gas flows from the lungs of the patient through the main tube 4, past the diaphragm valve 17 (the arrow 18) and out through the overpressure valve 23. It is realized that the end expiratory pressure here can be set by adjusting the opening pressure of the overpressure valve 23. The patient has still the possibility simultaneously to breathe spontaneously in the same manner as in the arrangement according to FIG. 1, whereby the inhalation takes place through the nonreturn valve 9, whereas the exhalation takes place through the exhalation valve 23. If for some reason the ventilation device 15 should not function but should choke the exhalation passage, just described, the exhalation can take place through the overpressure valve 11 in the branch tube 5.

One can easily and quickly switch from such an intermittent ventilation of the patient by means of the lung ventilator 3 to a CPAP treatment, simply by shifting the outfeed valve 3a from the ventilator 3 to being permanently open, so that the patient will continuously be supplied with the breathing gas. Hereby, the patient will be breathing spontaneously and inhale the breathing gas from the ventilator 3 via the branch tube 5 and exhale through the exhalation valve 23, the setting of which thus determines the pressure for the CPAP treatment.

If manual ventilation of the patient is desired, the sut-off valve 20 is opened, so that the rubber bag 21 is put in connection with the upper end of the main tube 4 via the diaphragm valve 17. Thus, when the rubber bag 21 is compressed, gas is pressed past the diaphragm valve 17 (the arrow 19) into the main tube 4 and thereafter down into the lungs of the patient. When the rubber bag 21 is thereupon released, the diaphragm valve 17 automatically changes its position, so that gas may flow out from the lungs of the patient past the diaphragm valve 17 (the arrow 18) and out through the exhalation valve 23. Simultaneously new gas or air is sucked into the rubber bag 21 through the nonreturn valve 22. Thus one obtains a manual ventilation of the patient carried out in the usual way, whereby this manual ventilation can be accomplished simultaneously with the automatic intermittent ventilation by the lung ventilator 3, without any conflict occuring between the two ventilations.

If one should wish to insert any instrument into the trachea of the patient, this can be done by temporarily removing the valve device 15 from the upper end 4b of the main tube, whereafter the desired instrument easily can be inserted down into the trachea of the patient through the main tube 4, and simultaneously the ventilation of the patient by means of the ventilator 3 is going on.

If one does not wish to have the possibility of ventilating the patient manually, the rubber bag 21 with the suction valve 22, the manual shut-off valve 20 and the diaphragm valve 17 can of course be left out, so that the valve device 15 will only comprise the adjustable exhalation valve 23.

It is evident that even more modifications of the arrangements shown in FIGS. 1 and 2 and described above, are possible within the scope of the invention. Thus the manually operated shut-off valve 20 in the device according to FIG. 2 may be substituted by a spring-loaded nonreturn valve, which opens only when the pressure inside the rubber bag 21 exceeds the pressure in the remaining part of the valve housing by a predetermined value, when the rubber bag is compressed. Furthermore there are naurally other designs of the connection part between the main tube 4 and the branch tube 5 which give the desired pneumatic valve function described above. Finally, the connection piece 1 could form a part of the endotracheal tube 2, instead of being detachably connected with it.

I claim:

1. A device for the ventilation of a patient comprising:
   an elongated main tube having a bore completely therethrough, said main tube connectable at a first end to a tube insertable into a patient;
   a branch tube for conveying breathing gas from a lung ventilator gas source, said branch tube having a bore completely therethrough and attached at a first end to the mid portion of said main tube with said branch tube bore in fluid communication with said main tube bore at a valveless junction, said branch tube extending in the direction of the other end of said main tube at an acute angle with said main tube;
   a three arm valve housing detachably mounted at a first arm to said other end of said main tube;
   a second arm of said valve housing comprising an overpressure valve having variably adjustable opening pressure;
   a rubber bag for manual ventilation being mounted on a third arm of said valve housing;
   said valve housing comprising a two-phase three-way valve means in selective communication with said overpressure valve and said rubber bag, said valve means for being in a first position only when said rubber bag is compressed for permitting flow of gas from said rubber bag into said main tube and otherwise for being in the other position for permitting flow of gas from said main tube through said second arm to said overpressure valve.

2. A patient ventilation device as claimed in claim 1 further comprising a nonreturn valve means for permitting an inflow of air from the surrounding atmosphere into at least one of said main tube and said branch tube and a second overpressure valve means for permitting out-flow of gas from said main tube to the surrounding atmosphere.

* * * * *